US00PP28341P3

(12) United States Plant Patent
Larse

(10) Patent No.: US PP28,341 P3
(45) Date of Patent: Aug. 29, 2017

(54) STRAWBERRY PLANT NAMED 'YOLI'

(50) Latin Name: *Fragaria×ananassa*
Varietal Denomination: Yoli

(71) Applicant: John Larse, Aptos, CA (US)

(72) Inventor: John Larse, Aptos, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 14/545,384

(22) Filed: Apr. 29, 2015

(65) Prior Publication Data

US 2016/0324049 P1 Nov. 3, 2016

(51) Int. Cl.
*A01H 5/08* (2006.01)

(52) U.S. Cl.
USPC ..... Plt./209

(58) Field of Classification Search
USPC ..... Plt./209
See application file for complete search history.

*Primary Examiner* — Anne Grunberg
(74) *Attorney, Agent, or Firm* — Cooley LLP

(57) ABSTRACT

The present invention provides a new and distinct strawberry plant designated as 'Yoli' (a.k.a. '104522').

6 Drawing Sheets

Latin name of the genus and species: *Fragaria×ananassa.*
Varietal denominations: 'Yoli' (a.k.a. '104522').

BACKGROUND OF THE INVENTION

The present invention relates to a new and distinct strawberry variety designated as 'Yoli' (a.k.a. '104522').

'Yoli' (a.k.a. '104522') is the result of a controlled-cross between a female parent cultivar designated 1621 and a male parent cultivar designated 1285 (both unpatented, proprietary cultivars) made by the Inventor and was first fruited in Watsonville, Calif. growing fields. Following selection and during testing, the plant was originally designated '104522' and subsequently named 'Yoli'.

This new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduces true to type in successive generations of asexual reproduction.

BRIEF SUMMARY OF THE INVENTION

This invention relates to new and distinctive strawberry cultivar designated as 'Yoli'. These cultivars are primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish strawberry variety 'Yoli' from known strawberry varieties. In addition, this new cultivar was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The fruit produced by this new cultivar is attractive and of excellent quality.

DESCRIPTION OF THE DRAWINGS

The accompanying color photographs depict various characteristics of the cultivars as nearly true as possible to make color reproductions.

DETAILED DESCRIPTION OF THE INVENTION

'Yoli' (a.k.a. '104522')

Figure 1:
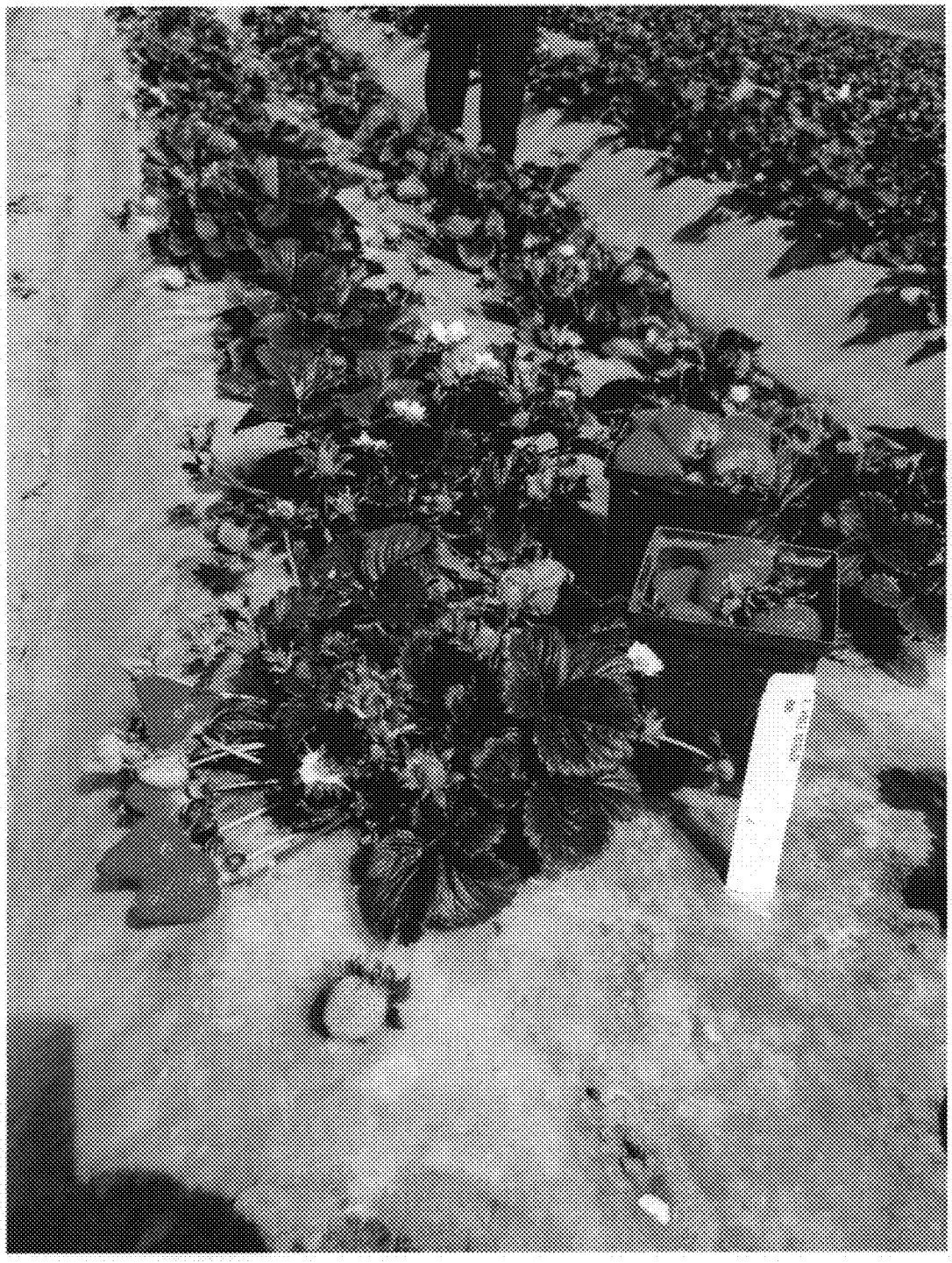
FIG. 1 shows 'Yoli' plants growing in the field.
Figure 2:
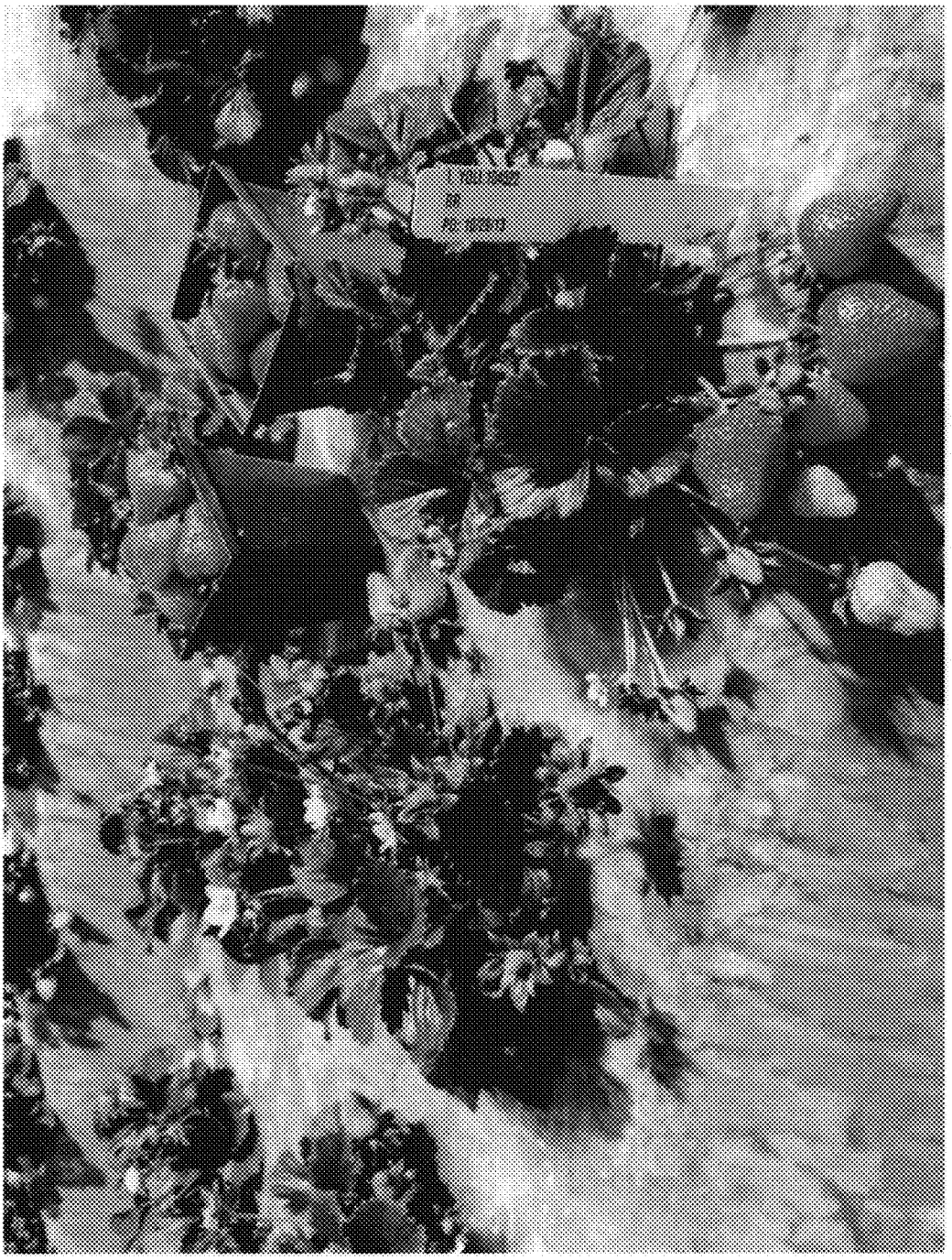
FIG. 2 shows inflorescences and fruits of 'Yoli' plants.
Figure 3:
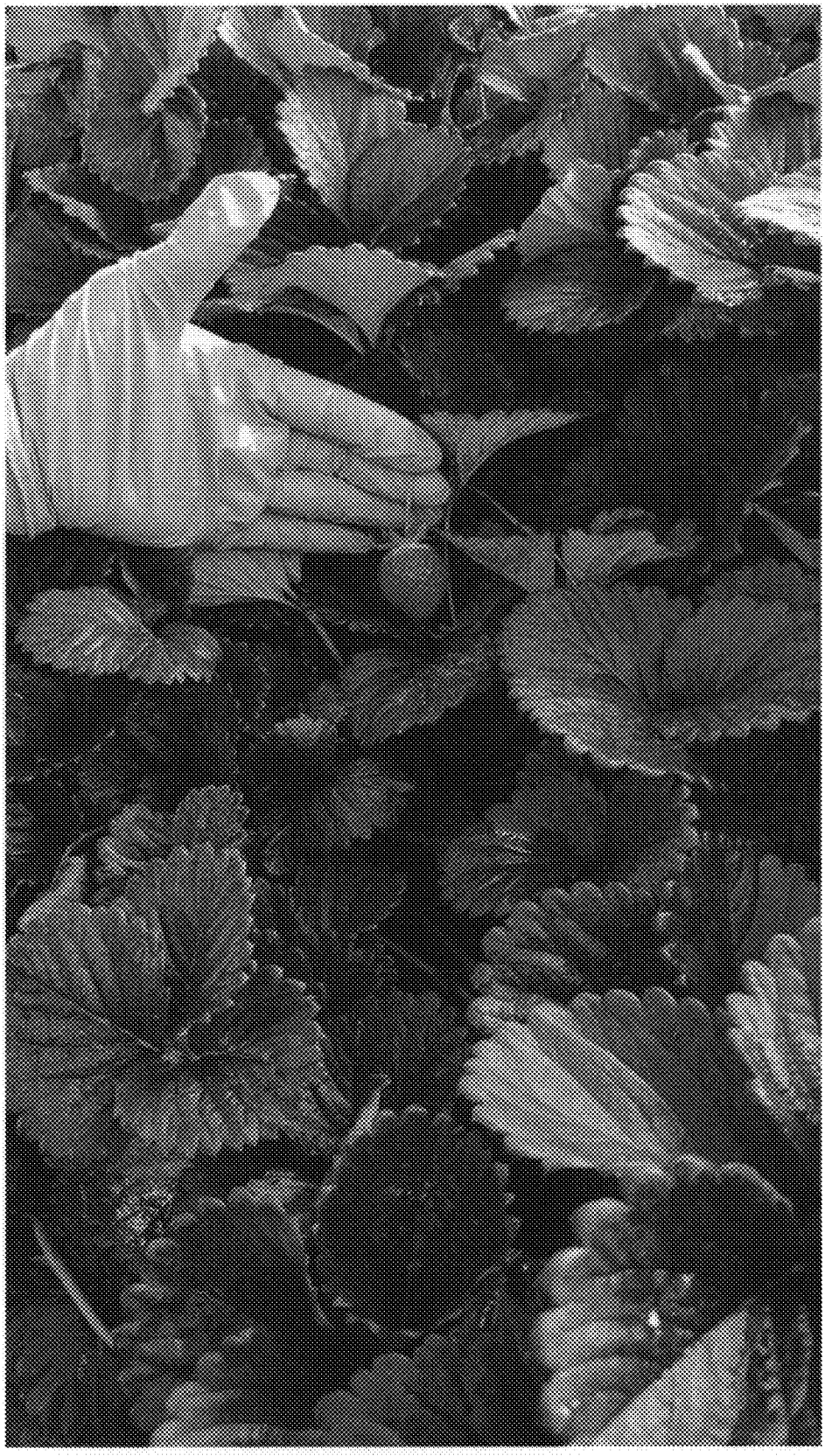
FIG. 3 shows 'Yoli' plants with near-mature fruit.
Figure 4:
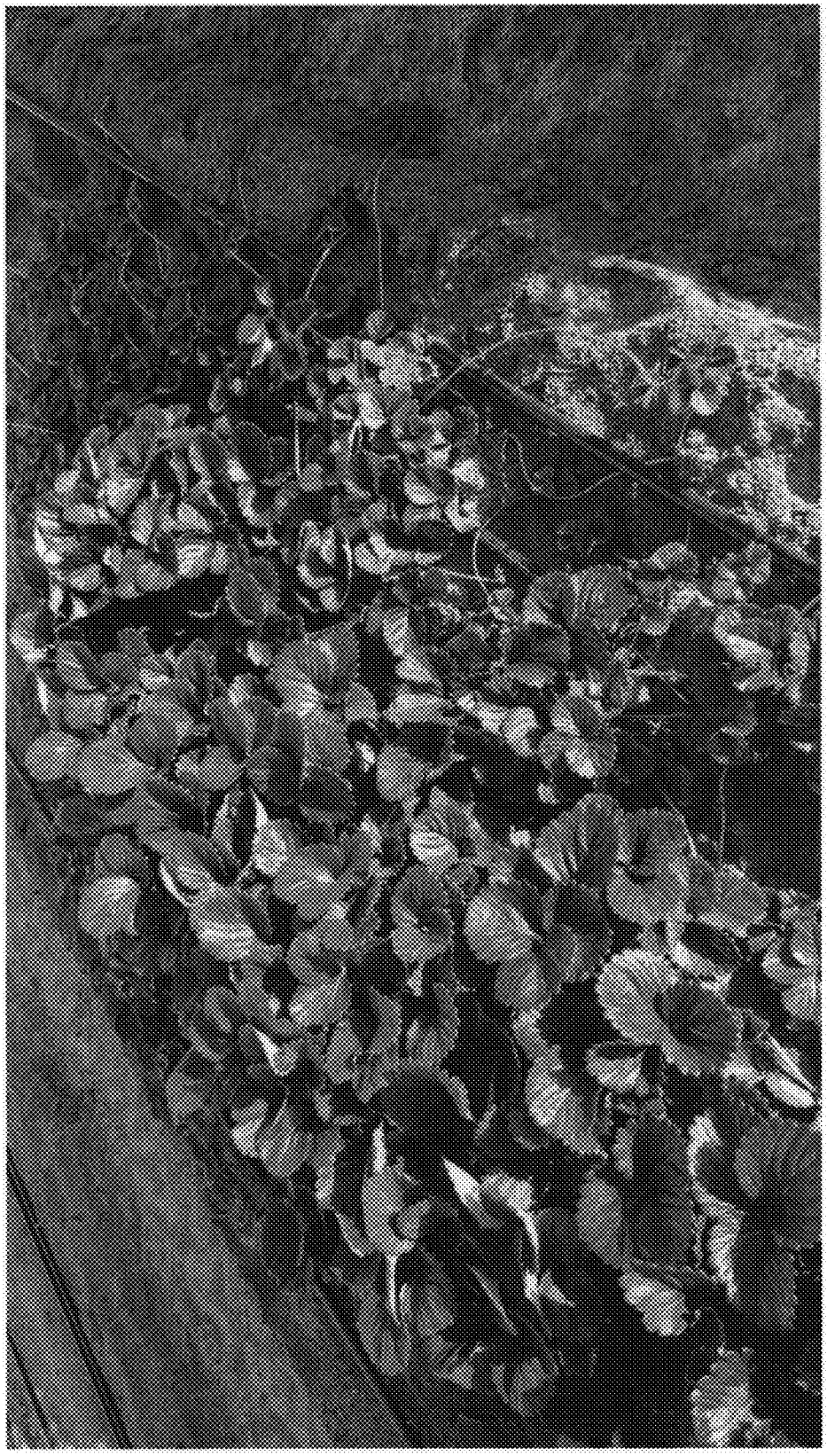
FIG. 4 shows 'Yoli' plants with runners growing in the field.
Figure 5:
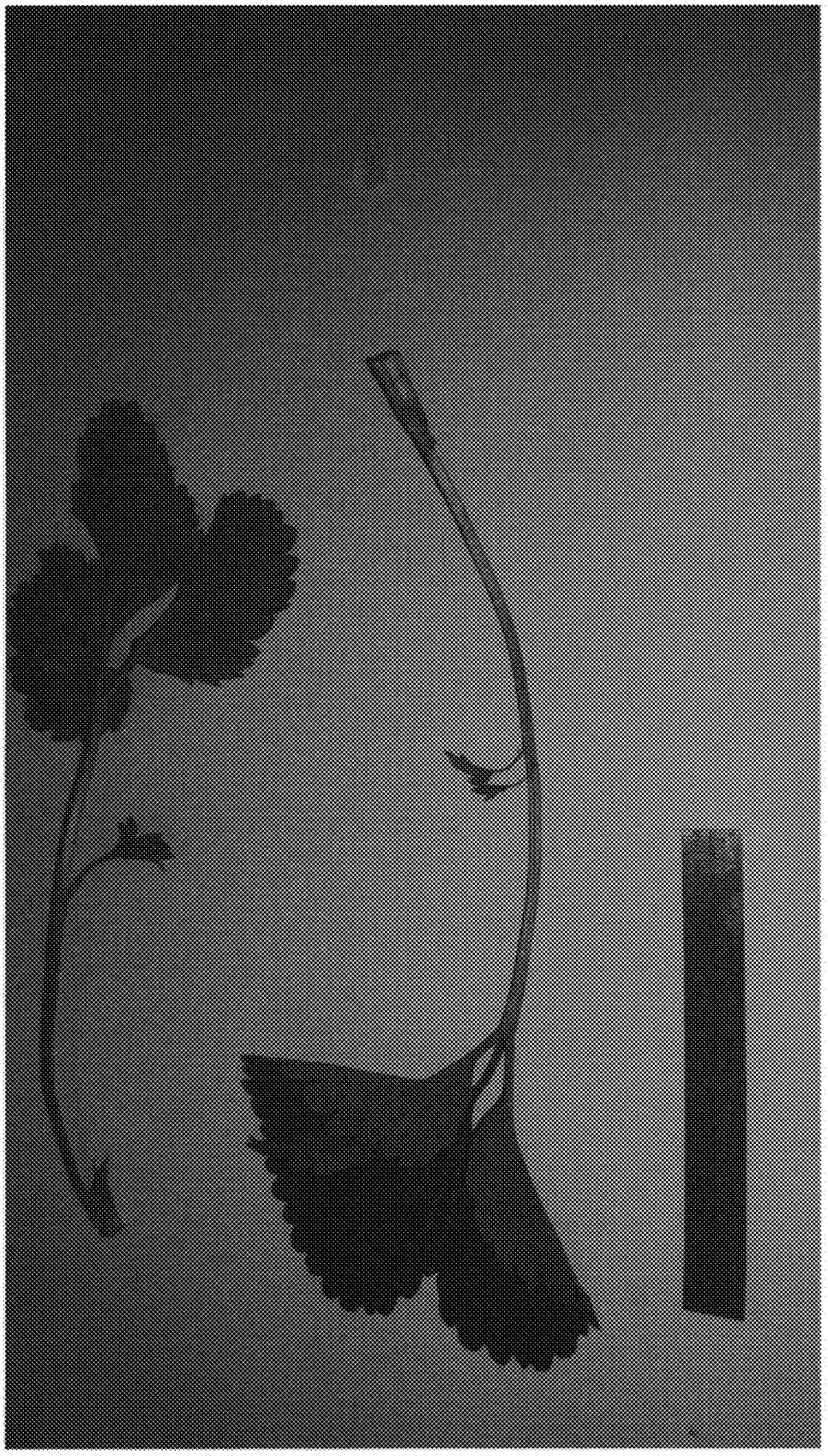
FIG. 5 shows petiole leaf of 'Yoli' plants.
Figure 6:
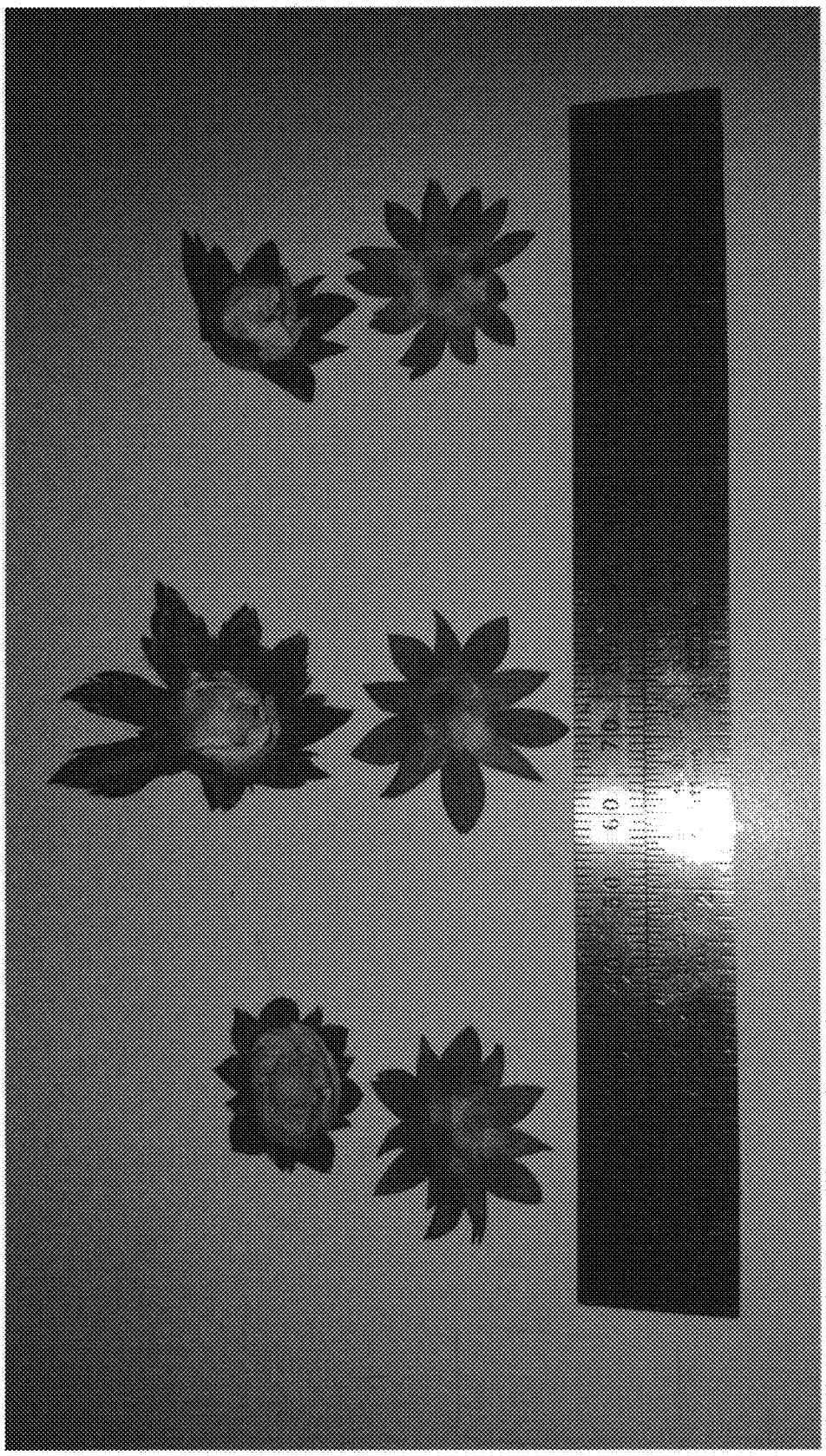
FIG. 6 shows the flower and calyx of 'Yoli' plants.

This invention relates to a new and distinctive day-neutral type cultivar designated as 'Yoli'. It is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits in combination distinguish strawberry variety 'Yoli' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

'Yoli' has not been observed under all possible environmental conditions, and the phenotype may vary significantly with variations in environment.

Hybrid Patent Data Sheet
(planted: October Year 1; measurement: November, Year 2)
'Yoh' (a.k.a. '104522')

| Plant | |
|---|---|
| Plant Growth Habit | semi-upright |
| Day length | neutral |
| Plant season | fall |
| Height (mm) | 310 |
| Diameter (mm) | 430 (the entire plant structure, including the "superstructure" of petioles, leaves, flowers)<br>60 (inner "base" or "heart" structure of the plant, i.e. the mature apical and axial crowns of the strawberry plant where petioles, flowers and runners are attached) |
| Density of foliage | medium |
| Plant vigor | moderate to high |
| Rain/weather tolerance | moderate |
| Harvest Ease | moderate |
| **Terminal Leaf** | |
| Length (mm) | 90 |
| Width (mm) | 90 |
| Terminal leaflet length/width ratio | 1 |
| Blistering | none |
| Terminal Leaflet shape | orbicular |
| Number of teeth per terminal leaflet | 20-22 |
| Shape of the terminal leaflet base | obtuse |
| Shape of teeth | obtuse |
| shape of terminal leaflet in cross-section | concave |
| margin description of the terminal | serrate |
| Color of upper side of leaves | 136A |
| Color of lower side of leaves | 137C |
| Leaf glossiness | medium to strong |
| Presence or absence of any leaf variegation | absence |
| No. of leaflets: | 62 |
| Terminal Leaflet margin | revolute |
| Terminal Leaflet shape of apex | rounded |
| **Petiole** | |
| Length (mm) | 244 |
| Width (mm) | 3.9 |
| Petiole pubescence | medium |
| Petiole pose of hairs | outwards |
| Petiole color | 145B |
| **Petiolule** | |
| Length (mm) | 28 |
| Width(mm) | 2.6 |
| **Stolon** | |
| Count (mm) | 43 |
| Diameter (mm) | 3 |
| Widest diameter of stolon at point of attachment of leaf (mm) | 4.1 |
| Density of pubescence on the stolon | medium |
| Stolon number | 8 |
| Stolon thickness | medium to large |
| Stolon color | 145A |
| Stolon anthocyanin | absent |
| **Inflorescence** | |
| Petal/flower | |
| Corolla (mm) | 25 |
| Calyx (mm) | 25 |

-continued

Hybrid Patent Data Sheet
(planted: October Year 1; measurement: November, Year 2)
'Yoh' (a.k.a. '104522')

| | |
|---|---|
| Calyx diameter relative to corolla | 1 |
| Position of calyx | even |
| Color of calyx | 137A |
| Pose of calyx segments | spreading |
| Size of calyx in relation to fruit | smaller |
| Petal length (mm) | 13 |
| Petal width (mm) | 13 |
| Petal length/width ratio | 1 |
| Petal number per flower | 5-6 |
| Sepal length (mm) | 9 |
| Sepal width (mm) | 6 |
| Sepal number per flower | 10-15 |
| Peduncle size | Medium to long |
| Stipules length (mm) | 35 |
| Stipules width (mm) | 11 |
| Stipule pubescence | medium |
| Stipule anthocyanin | mild presence |
| Stipule color | 145B to 181D |
| Pedicel color | 145A |
| Attitude of hairs on petiole and pedicel | horizontal |
| Inflorescence position relative to foliage | even to above foliage |
| flower arrangement of petals | overlapping |
| Number of flowers per plant | ~20 |
| Flower size | medium |
| Petal shape | orbicular |
| Petal apex | rounded |
| Petal margin | entire |
| Petal base shape | concave |
| Petal spacing | overlapping |
| Upper and lower Petal color | 155C |
| Sepal Shame | elliptical |
| Sepal apex | convex |
| Number of stamen | 22 |
| Receptacle color | 4A |
| Anther color | 14A |
| Fertility | Self-fertile |
| **Fruit** | |
| Fruit/truss | 2-5 |
| Fruit truss length (mm) | 235 |
| Fruiting truss diameter (mm) | 21.7-26.7 |
| Fruit truss attitude | Erect |
| Truss color | 145A |
| Length (mm) | 47 |
| Width (mm) | 39 |
| Fruit length/width ratio | 1.2 |
| Core length (mm) | 30 |
| Core width (mm) | 14 |
| Glossiness | medium |
| Fruit skin color | 41A |
| Fruit weight (g) | 21 |
| Predominant fruit shape | long-conical |
| Difference in shape between primary & secondary fruits | none to very slight |
| Width of band without of achenes (mm) | 2 |
| Position of achenes | even to above |
| Achene color | 145A |
| Achenes per fruit | 275 |
| Achene weight (g) | 0.25 |
| Firmness of flesh | soft to firm |
| Color of the flesh | 41A |
| Evenness of flesh color | even to slightly uneven |
| Grams of fruit/plant (During peak season, June) | 497 |
| Appearance Score (from 1-5, with 5 = best) | 4.5 |
| Storage longevity | 9 to 13 days |
| Cull rate: Non salable fruit production rate | <25% |

-continued

| Hybrid Patent Data Sheet<br>(planted: October Year 1; measurement: November, Year 2)<br>'Yoh' (a.k.a. '104522') | |
|---|---|
| Disease and pest resistance | Not tested |
| Acidity as measured by pH | NA |
| Sweetness as measured by brix | NA |

(NA: Not Available)

When 'Yoli' is compared to 'Seascape' (U.S. Plant Pat. No. 07,614), 'Yoli' has a margin of terminal leaflet that is serrate, while the margin of the terminal leaflet of 'Seascape' is crenate. In addition, the leaf glossiness of 'Yoli' ranges from medium to strong, while the leaf glossiness of 'Seascape' is medium. The number of leaflets of 'Yoli' is 62, while the number of leaflets of 'Seascape' is 49. 'Yoli' also has a smaller fruit, higher yield when compared to 'Seascape', and the flowers of 'Yoli' are always presenting above foliage.

The invention claimed is:

1. A new and distinct cultivar of strawberry plant named 'Yoli' substantially as shown and described herein.

* * * * *